United States Patent [19]

Adams et al.

[11] Patent Number: 5,098,921

[45] Date of Patent: Mar. 24, 1992

[54] NITRO-SUBSTITUTED AROMATIC OR HETERO-AROMATIC COMPOUNDS FOR USE IN CANCER TREATMENT

[75] Inventors: Gerald E. Adams, Wheatley; Edward M. Fielden, Blewbury; Terence C. Jenkins, North Cheam; Ian J. Stratford, Farringdon, all of England

[73] Assignee: National Research Development Corporation, London, England

[21] Appl. No.: 279,091

[22] Filed: Dec. 2, 1988

[30] Foreign Application Priority Data

Dec. 4, 1987 [GB] United Kingdom ............... 8728418
Aug. 2, 1988 [GB] United Kingdom ............... 8818348

[51] Int. Cl.$^5$ ............... A01N 43/64; A61K 31/41; C07D 249/17; C07D 233/00
[52] U.S. Cl. ............... 514/383; 514/385; 548/264.8; 548/300
[58] Field of Search ............... 548/300, 264.8; 514/383, 385

[56] References Cited

U.S. PATENT DOCUMENTS

4,323,689 4/1982 Vogel et al. ............... 209/959

FOREIGN PATENT DOCUMENTS

| 928 | 3/1979 | European Pat. Off. |
| 30332 | 6/1981 | European Pat. Off. |
| 1257238 | 12/1971 | United Kingdom |
| 1425293 | 2/1976 | United Kingdom |
| 2003154 | 3/1979 | United Kingdom |
| 2123816 | 2/1984 | United Kingdom |
| 2131020 | 6/1984 | United Kingdom |

OTHER PUBLICATIONS

Int. J. Radiat. Biol. (1972), vol. 21, No. 5, pp. 475-482, (J. D. Chapman et al).
Biochemical Pharmacology vol. 35, No. 7, pp. 1107-1112 (1986), (A. R. Silver and P. O'Neill).
J. Chem. Soc. Faraday Trans. I, 72, 1377-1390 (1976), (P. Wardman and E. D. Clarke).
Cancer Research, 32, pp. 2616-2624, Dec. 1972, (J. D. Chapman et al).

Primary Examiner—C. Warren Ivy
Assistant Examiner—Raymond Covington
Attorney, Agent, or Firm—Oblon, Spivak, McClelland, Maier & Neustadt

[57] ABSTRACT

A compound for treating a patient having a solid tumor in which it is known or suspected that hypoxic cells are present, which is a compound of formula (A):

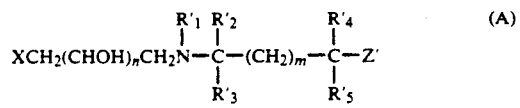

wherein X represents a nitro-substituted aromatic or hetero-aromatic group with a one-electron reduction potential at pH 7 of from $-250$ to $-500$ mV; each of $R'_1$ to $R'_5$ independently represents hydrogen or an alkyl, hydroxyalkyl, aryl, aralkyl or alkaryl group; m is 0 or 1; n is 1 or 2; and Z' represents a leaving group which has the potential for expulsion via an intramolecular cyclization reaction; or a physiologically acceptable acid addition salt thereof.

20 Claims, No Drawings

NITRO-SUBSTITUTED AROMATIC OR HETERO-AROMATIC COMPOUNDS FOR USE IN CANCER TREATMENT

This invention relates to nitro-substituted aromatic and hetero-aromatic compounds useful in cancer treatment. More particularly, it relates to such compounds useful in the treatment of cancer patients by radiotherapy or chemotherapy.

GB-A-2 123 816 is concerned with the nitroimidazoles of formula (I):

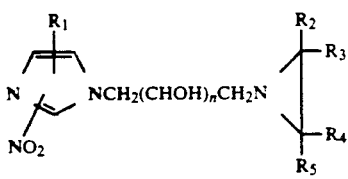

in which $R_1$ represents hydrogen or an alkyl group such $C_1$–$C_6$ alkyl; $R_2$–$R_5$ represent hydrogen, alkyl such as $C_1$–$C_6$ alkyl, aryl, aralkyl or alkaryl; and n is 1 or 2. These compounds are useful in increasing the sensitivity of tumour cells to radiation in radiotherapy and also in potentiating or enhancing damage to tumours by chemotherapeutic agents. A variety of processes are disclosed for the preparation of these compounds, including cyclising a compound of formula (VII):

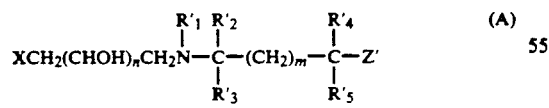

in which $R_1$–$R_5$ and n are as defined above and Z represents halogen, typically bromine or chlorine. However, no specific compounds with this formula are identified.

We have now found that compounds of formula (VII) can act as radiosensitisers and bioreductive agents in their own right, as may analogues of these compounds. They exhibit differential hypoxic cytotoxicity and may act as chemopotentiators. Accordingly, the present invention provides compounds for use in treating cancer, in particular for treating a patient having a solid tumour in which it is known or suspected that hypoxic cells are present, which have the formula (A):

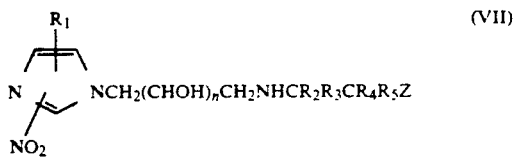

wherein X represents a nitro-substituted aromatic or hetero-aromatic group with a one-electron reduction potential at pH 7 ($E_7^1$; Wardman and Clarke, *J Chem Soc Faraday Trans I* 72 1377–1390 (1976)) of from −250 to −500 mV; each of $R'_1$ to $R'_5$ independently represents hydrogen or an alkyl, hydroxyalkyl, aryl, aralkyl or alkaryl group; m is 0 or 1; n is 1 or 2; and Z' represents a leaving group which has the potential for expulsion via an intramolecular cyclisation reaction; and physiologically acceptable acid addition salts thereof.

Certain classes of these compounds are novel. The invention therefore also provides compounds of formula (B):

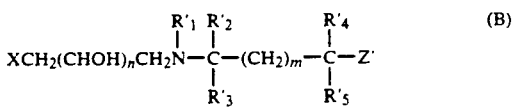

wherein X, $R'_1$ to $R'_5$, m, n and Z' are as defined above with the proviso that m is 1 when X represents

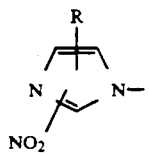

in which R is hydrogen or an alkyl group, $R'_1$ is hydrogen, each of $R'_2$ to $R'_5$ independently represents hydrogen, alkyl, aryl, aralkyl or alkaryl and Z' represents halogen and when X represents:

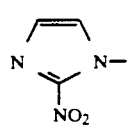

each of $R'_1$ to $R'_5$ is hydrogen and Z' is

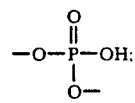

and physiologically acceptable acid addition salts thereof.

Preferably Z' in formulae (A) and (B) is not a negatively-charged group such as phosphate. Indeed, preferably the compounds of formulae (A) and (B) are not negatively-charged but are uncharged.

An alkyl group is typically a $C_1$–$C_6$ group, preferably methyl. A hydroxyalkyl group is typically a hydroxy ($C_1$–$C_6$ alkyl) group such as hydroxymethyl. An aryl group is typically phenyl. An aralkyl group is typically a phenyl ($C_1$–$C_6$) alkyl group such as benzyl. An alkaryl group is typically a ($C_1$–$C_6$) alkyl phenyl group such is methyl-substituted Novel individual compounds are:
1-(2-nitro-1-imidazolyl)-3-(2-chloroethylamino)-2-propanol hydrochoride,
1-(2-nitro-1-imidazolyl)-3-(2-bromoethylamino)-2-propanol hydrobromide,
1-(2-nitro-1-imidazolyl)-3-(2-iodoethylamino)-2-propanol hydriodide,
1-(2-nitro-1-imidazolyl)-3-(2-fluoroethylamino)-2-propanol hydrochoride,
1-(2-nitro-1-imidazolyl)-3-(2-acetoxyethylamino)-2-propanol,
1-(2-nitro-1-imidazolyl)-3-(2-trifluoroacetoxyethylamino)-2-propanol,
1-(2-methyl-4-nitro-1-imidazolyl)-3-(2-chloroethylamino)-2-propanol hydrochoride,
1-(2-methyl-4-nitro-1-imidazolyl)-3-(2-bromoethylamino)-2-propanol hydrobromide, 1-(2-methyl-4-nitro-1-imidazolyl)-3-(2-iodoe-
thylamino)-2-propanol hydriodide,
1-(2-methyl-5-nitro-1-imidazolyl)-3-(2-chloroe-
thylamino)-2-propanol hydrochoride,
1-(2-methyl-5-nitro-1-imidazolyl)-3-(2-bromoe-
thylamino)-2-propanol hydrobromide,
1-(2-methyl-5-nitro-1-imidazolyl)-3-(2-iodoe-
thylamino)-2-propanol hydriodide,
1-(2-methyl-5-nitro-1-imidazolyl)-3-(2-fluoroe-
thylamino)-2-propanol hydrochoride,
1-(3-nitro-1,2,4-triazol-1-yl)-3-(2-chloroethylamino)-
2-propanol hydrochoride,
1-(3-nitro-1,2,4-triazol-1-yl)-3-(2-bromoethylamino)-
2-propanol hydrobromide,
1-(2-nitro-1-imidazolyl)-3-(3-bromopropylamino)-2-
propanol hydrobromide,
1-(2-nitro-1-imidazolyl)-3-(1-chloro-2-methyl-2-
propylamino)-2-propanol hydrochloride,
1-(2-nitro-1-imidazolyl)-3-(1-bromo-2-methyl-2-
propylamino)-2-propanol hydrobromide,
1-(2-nitro-1-imidazolyl)-3- (dl-threo-2-chloro-3-
butylamino)-2-propanol hydrochloride,
1-(2-nitro-1-imidazolyl)-3-(dl-threo-2-bromo-3-
butylamino)-2-propanol hydrobromide,
1-(2-nitro-1-imidazolyl)-3-(2-chloro-2,3-dimethyl-3-
butylamino)-2-propanol hydrochloride, and
1-(2-nitro-1-imidazolyl)-3-(2-bromo-2,3-dimethyl-3-
butylamino)-2-propanol hydrobromide.

Group X is a mononitro-substituted ring It may also be substituted by an alkyl group, preferably a $C_1-C_6$ alkyl group such as methyl. The ring is preferably a 5- or 6-membered ring incorporating one, two or three nitrogen atoms in the ring. More preferred are the groups:

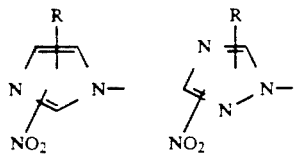

wherein R is hydrogen or an alkyl group such as $C_1-C_6$ alkyl. Preferred novel classes of compounds are therefore compounds of formula (C) and (D):

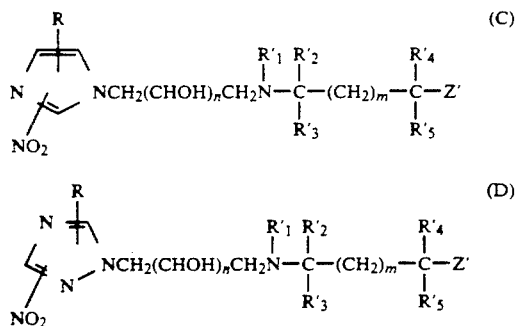

wherein R, R'$_1$ to R'$_5$, Z', m and n are as defined above with the proviso that m is 1 when R'$_1$ is hydrogen, each of R'$_2$ to R'$_5$ independently represents hydrogen, alkyl, aryl, aralkyl or alkaryl and Z' represents halogen in formula (C), and physiologically acceptable acid addition salts thereof.

When R is alkyl, it is preferably a $C_1-C_6$ alkyl group and more preferably a methyl group. Preferred values for R are hydrogen and methyl. The nitro group is preferably in the 2-position when X represents an imidazol-1-yl group or in the 3-position when X represents a 1,2,4-triazol-1-yl group. The preferred value for m is 0 and for n is 1.

R'$_1$ to R'$_5$ are each preferably independently hydrogen or $C_1-C_6$ alkyl. The preferred alkyl group is methyl. Preferred are compounds in which R'$_1$ is hydrogen and each of R'$_2$ to R'$_5$ is independently hydrogen or methyl. Examples of such compounds are those in which R'$_1$ is hydrogen and R'$_2$ to R'$_5$ are each hydrogen or R'$_2$ to R'$_3$ are hydrogen and R'$_4$ and R'$_5$ are methyl or R'$_2$ and R'$_4$ are methyl and R'$_3$ and R'$_5$ are hydrogen or R'$_2$ and R'$_3$ are methyl and R'$_4$ and R'$_5$ are hydrogen or and R'$_2$ to R'$_5$ are each methyl.

Z' represents a leaving-group function which has the potential for expulsion via an intramolecular cyclisation reaction. For example, Z' may be halogen; $—OCOR_6$, $—OSOR_6$, $—OSO_2R_6$, $—OPO_3(R_6)_2$, or $—OP(O)(N(R_6)_2)_2$ where $R_6$ is hydrogen, alkyl, haloalkyl, aryl, aralkyl, thioalkyl, acyl or amino; or aryloxy, $—ONO_2$, $—NHSO_2R_7$, $—NHCOR_7$, $—NHCO_2R_7$, $—N(COR_7)_2$ or cyclic imide where $R_7$ is hydrogen, alkyl, aryl or aralkyl; or $—N^+R^aR^bR^c$ or $—N(O)R^aR^b$ where $R^a$ to $R^c$ are independently alkyl or a N-heterocycle such as pyridine or imidazole.

From amongst these, Z' typically may be halogen or acyloxy unsubstituted or substituted by halogen. Preferred are halogen, $C_1-C_6$ alkanoyloxy and per- or poly-fluoro-$C_2-C_6$ alkanoyloxy. More preferred are fluorine, chlorine, bromine, iodine, acetoxy and trifluoroacetoxy. Most preferred is bromine.

Acid addition salts of the compounds of formula (A) may be salts with any physiologically acceptable acid. Examples of suitable acids are inorganic acids such as hydrochloric, hydrobromic and hydriodic acid. Organic acids may be used. Preferred are hydrohalic acids in which the halogen anion corresponds to the halogen denoted by the group Z', although this is not essential. Particularly preferred compounds are 1-(2-nitro-1-imidazolyl)-3-(2-bromoethylamino)-2-propanol and its salts especially the hydrobromide.

A variety of ways can be used to prepare a compound of formula (A). A compound of formula (E):

wherein X, m, n and R'$_2$ to R'$_5$ are as defined above, may be reacted with a compound of formula (F):

wherein Z' is as defined above. Compounds of formula (A) in which R'$_1$ is hydrogen are thus prepared. Reaction is typically effected in the presence or absence of an inert organic solvent. When an inert organic solvent is used, this may suitably be a $C_1-C_4$ alkanol (e.g. methanol or ethanol), 2-propanone or other low-boiling alkanone, N,N-dimethylformamide or -acetamide, or the like. Alternatively, an excess of the reagent of formula (F) may be used, either as the solvent or as an aqueous solution. When water is employed as cosolvent or as the solvent for one of the reagents, products due to hydrolysis of compound (E) are also formed. The reaction may be carried out at from 0° C. to room temperature. The use of elevated temperatures may lead to partial polymerisation, and hence lowered product yields. In a preferred procedure, the reaction is carried out at a temperature of from 0 to 10° C. using 2-propanone as solvent and 2.0 or more mol equivalents of compound (F).

Another process for the preparation of compounds of formula (A) in which Z' is halogen is via selective or partial halogenation of a compound of formula (G):

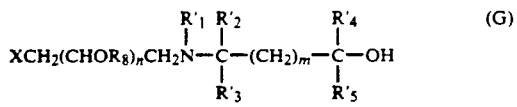

wherein X, m, n and $R'_1$ to $R'_5$ are as defined above and $R_8$ is hydrogen or an O-protecting function (e.g. 2-tetrahydropyranyl ether or tert-butyldimethylsilyl ether), and subsequent removal of the hydroxy protecting group, if present. Halogenation may be effected using a variety of conventional halogenating reagents. Treatment of a compound of formula (G) with, for example, chlorotrimethylsilane and sodium iodide in acetonitrile solution by a standard procedure (*Synthesis* 1979 379; *J Org Chem* 1979 44 1247) provides compounds of formula (A) where Z' is iodine. Analogous treatment of compound (G) with bromotrimethylsilane using a literature method (*Tetrahed Letters* 1978 4483) affords compounds of formula (A) where Z' is bromine. Reaction of the alcohol (G) with hexachloro-2-propanone and triphenylphosphine in sulpholane solution using a general method (see, e.g. *J Org Chem* 1981 46 824) gives compounds of formula (A) where Z' is chlorine.

In a preferred process, a compound of formula (G) is treated with a stoichiometric quantity of dimethylbromosulphonium bromide in N,N-dimethylformamide solution at 50° C. to yield a compound of formula (A) in which Z' is bromine. In a second preferred process, a compound of formula (G) is heated to 50° C. with 1.5 mol equivalents each of N-bromosuccinimide and triphenylphosphine in N,N-dimethylformamide solution to give a compound of formula (A) in which Z is bromine.

Further, compounds of formula (A) can be prepared by reacting a compound of formula (H) or (J):

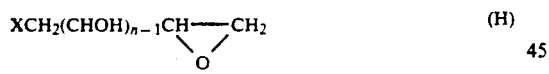

wherein X and n are as defined above and Q is typically chlorine or bromine, with a compound of formula (K):

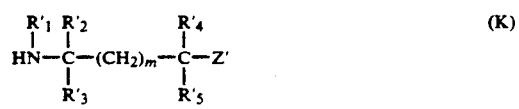

wherein m, $R'_1$ to $R'_5$ and Z' are as defined above, or an acid addition salt thereof. The reaction is typically effected in the presence or absence of an inert organic solvent. When an inert organic solvent is used, this may suitably be a $C_1$–$C_4$ alkanol (e.g. methanol or ethanol), N,N-dimethylformamide or -acetamide, or similar. Reactions involving condensation of compounds (J) and (K) may be accelerated by the use of 1 mol equivalent of an acid-binding agent such as an alkali-metal carbonate (e.g. sodium or potassium carbonate) or a tertiary organic amine (e.g. pyridine or triethylamine). The use of 2 mol equivalents of compound (K) is preferred in such a reaction. The reaction may be carried out at room temperature or at an elevated temperature. In a preferred process, the reaction is carried out in ethanol solution at reflux temperature, without using an acid-binding agent.

In another procedure, a compound of formula (L):

or its metal salt derivative (e.g. $X^-Na^+$), where X is as defined above, may be reacted with a compound of formula (M):

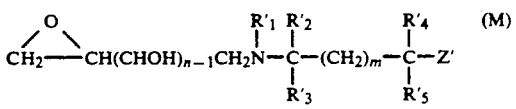

or, alternatively, with a compound of formula (N):

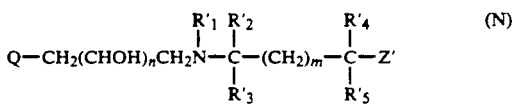

where m, n, $R'_1$ to $R'_5$, Q and Z' are as defined above. The reaction is typically effected in the presence or absence of an inert organic solvent. When an inert organic solvent is employed, this may suitably be a $C_1$–$C_4$ alkanol (e.g. methanol or ethanol), N,N-dimethylformamide or -acetamide, or similar. Reactions between compounds of formula (L) and (N) may be accelerated by the use of 1 mol of an added acid-binding agent, as discussed above. The use of 2 mol equivalents of the amine-compound (N) is to be preferred. Either reaction may be carried out at room temperature or at elevated temperatures, up to the boiling point of the solvent. In a preferred process, the sodio- or lithio-salt of a compound of formula (L) is condensed with an equimolar quantity of either (M) or (N) in methanol or N,N-dimethylformamide solution at 50° C.

In a further process, a compound of formula (O):

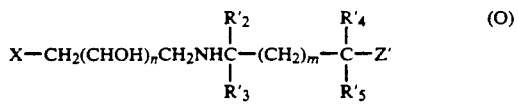

is converted to a compound of formula (P):

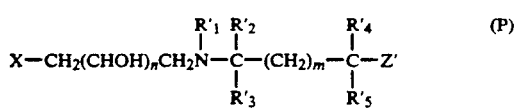

wherein m, n, $R'_1$ to $R'_5$, X and Z' are as defined above. This is typically achieved via N-alkylation or N-arylation by treatment with, for example, (i) a haloalkane (e.g. iodomethane, etc), haloalkylarene or haloarene at room temperature using either acetone or excess reagent as solvent (i.e. $R'_1$=alkyl, aralkyl or aryl); (ii) oxirane using the reagent as solvent or, alternatively, in methanol or ethanoic acid solution at 0–30° C. (i.e. $R'_1$=—$CH_2CH_2OH$); (iii) methanal/acetophenone (or other compound containing an active hydrogen atom)

by Mannich condensation using a conventional procedure (i.e. $R'_1 = -CH_2CH_2COC_6H_5$, or similar); (iv) methanal/sodium cyanotrihydridoborate by reductive alkylation using a standard procedure (see e.g. *Aldrichimica Acta* 1979 12(2) 34) (i.e. $R'_1 = -CH_3$).

Yet further compounds of formula (A) in which m is 1 and 0 respectively and Z' is halogen can be prepared by conversion of an unsaturated compound of formula (S):

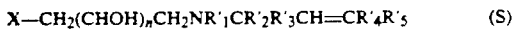

$$X-CH_2(CHOH)_nCH_2NR'_1CR'_2R'_3CH=CR'_4R'_5 \quad (S)$$

or a compound of formula (T):

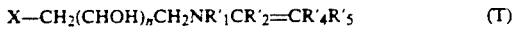

$$X-CH_2(CHOH)_nCH_2NR'_1CR'_2=CR'_4R'_5 \quad (T)$$

where X, n and $R'_1$ to $R'_5$ are as defined above. In a general procedure (*J Org Chem* 1981 46 2582, 3113; *Synth Comm* 1981 11 521), a compound of formula (S) or (T) is first reacted with di(cyclohexyl)borane and subsequently treated with chloramine-T, bromine or iodine monochloride to give a compound of formula (A) where Z is chlorine, bromine or iodine, respectively.

The compounds of formula (A) may be converted as desired into a physiologically acceptable acid addition salt thereof. Preferably, the compounds are isolated as such from the reaction mixture.

The compounds of formula (A) and their salts are useful in increasing the sensitivity of tumour cells to radiation in radiotherapy and as bioreductive agents. A compound is administered to a patient having a radiation treatable cancer, prior to or shortly after irradiation of the tumour, in an amount effective to increase the sensitivity of the tumour cells to the effects of the irradiation.

Any solid tumour, which may have regions where cells are radiobiologically hypoxic and become resistant to ionising radiation, may be treated. Examples of such tumours are epithelial tumours of the head, neck, thorax and abdomen, soft tissue sarcomas and brain tumours. The compounds of formula (A) and their salts can therefore be employed in the radiotherapy of all such solid tumours where hypoxic cells are known or suspected to exist.

The compounds of formula (A) and their salts may also be used where an agent having differential hypoxic cytotoxicity is required. The compounds can be employed for chemopotentiation of a chemotherapeutic agent or as a chemotherapeutic by administration of a compound (A) or salt thereof to a patient having a localised or metastatic cancer. Administration is generally carried out prior to simultaneously with or after administration of a chemotherapeutic agent such as melphalan, cyclophosphamide, 5-fluorouracil, adriamycin or CCNU(1-(2-chloroethyl)-3-cyclohexyl-1-nitrosourea). Any solid tumours, such as above, which are primary or secondary deposits, where it is known or suspected that hypoxic cells are present can therefore benefit from treatment employing a compound of formula (A) or salt thereof.

The compounds of formula (A) and salts thereof may be administered orally or intravenously. The amount administered depends on factors such as the cancer, the condition of the patient and the body weight of the patient. Typically, however, doses of 50 to 1000 mg/m² of a patient's body area may be employed.

A compound of formula (A) or a physiologically acceptable salt thereof may be formulated in a manner appropriate to the treatment for which it is to be used by bringing it into association with a pharmaceutically compatible carrier or diluent. The compound may be included in a dosage form such as a tablet or capsule, for example a capsule comprising known formulation components such as one or more of those described in Example A of GB-A-2 003 154. The compound may also be formulated for intravenous administration e.g. in a saline drip solution.

The invention therefore also provides a pharmaceutical composition comprising a compound of formula (A) or a physiologically acceptable salt thereof and a pharmaceutically compatible carrier or diluent. The composition must be sterile and pyrogen-free. It may be presented in unit dosage form.

The following Examples illustrate the invention.

EXAMPLE 1

1-(2-Nitro-1-imidazolyl)-3-(2-chloroethylamino)-2-propanol (RB-6144)

(a) A mixture containing 1-(2-nitro-1-imidazolyl)-3-(1-aziridino)-2-propanol (RSU-1069) prepared by the method of Adams et al. [Adams, G.E., Ahmed, I., Gibson, D. and Stratford, I.J., GB-A-2123816] (2.12 g, 10.0 mmol) and purified by recrystallisation [O'Neill, P., McNeil, S.S. and Jenkins, T.C., *Biochemical Pharmacology* 1987 36 1787-1792] and acetone (20 cm³) was warmed to 40° C. The resulting clear solution was cooled with stirring to 5°-10° C. using an external ice-water bath and treated with a saturated solution of hydrogen chloride in acetone (20 cm³). An exothermic reaction ensued. The reaction mixture was treated with decolourising charcoal (0.3 g), filtered whilst still warm and allowed to crystallise to give 1-(2-nitro-1-imidazolyl)-3-(2-chloroethylamino)-2-propanol hydrochloride (2.66 g, 93%) as a very pale yellow crystalline solid, m.p. 153°-154° C. (dec.). Recrystallisation from aqueous acetone afforded pale yellow prisms of unchanged melting point, after drying in vacuo ($P_2O_5$, 0.1 Torr, 25° C. for 72 hours).

Infra-red (KBr, cm$^{-1}$): 3450(br.sh., $NH_2^+$),3345(br., OH),3146+3090(imid.C-H),3030,3010,2975,2945,2880,2845,2770, 2680,2620,2560,2510,2420,1593,1542,1509,1495,etc.

Analysis for $C_8H_{14}N_4O_3Cl_2$ (M=285.13):
Calculated: C: 33.70; H: 4.95; N: 19.65; Cl: 24.87%.
Found: C: 33.91; H: 5.02; N: 19.64; Cl: 24.63%.

(b) A solution of 1-(2-nitro-1-imidazolyl)-3-(1-aziridino)-2-propanol(2.12 g, 10.0 mmol) in acetone (20 cm³) red as described in Example 1(a) was stirred at 0-5° C. using external ice-water cooling. Concentrated aqueous hydrochloric acid (38% w/w HCl, 2.0 cm³) was added in one portion. The mixture was treated with decolourising charcoal (0.3 g), filtered and chilled to give 1-(2-nitro-1-imidazolyl)-3-(2-chloroethylamino)-2-propanol hydrochloride (1.89 g, 66.3%) as a pale yellow microcrystalline solid, m.p. 152.5°-153.5° C. (dec.) after drying in vacuo.

EXAMPLE 2

1-(2-Nitro-1-imidazolyl)-3-(2-bromoethylamino)-2-propanol (RB-6145)

(a) In a manner analogous to that described in Example 1 (a) there was obtained by condensation of 1-(2-nitro-1-imidazolyl)-3-(1-aziridino)-2-propanol with anhydrous hydrogen bromide, 1-(2-nitro-1-imidazolyl)-3-

(2-bromoethylamino)-2-propanol hydrobromide in the form of a very pale yellow crystalline solid, m.p. 150.5°–151.5° C. (dec.); yield 96%.

Infra-red (KBr, cm$^{-1}$): 3450(br.sh.,NH$_2$+),3345(br.,OH),3160+3140+308-7(imid.C—H), 3045,3010,2975,2940,2930,2900,2835,2775,2760,2678,26-40, 2600,2540,2500,2418,1590,1539,1507, 1493,etc.

Analysis for C$_8$H$_{14}$N$_4$O$_3$Br$_2$ (M=374.05):
Calculated: C: 25.69; H: 3.77; N: 14.98; Br: 42.73%,
Found: C: 25.82; H: 3.80; N: 15.15; Br: 42.49%.

(b) In a manner analogous to that described in Example 1(b) there was obtained by reaction of 1-(2-nitro-1-imidazolyl)-3-(1-aziridino)-2-propanol with a small excess of aqueous hydrobromic acid (48% w/w HBr) at 0°–5° C. and recrystallisation from aqueous acetone, 1-(2-nitro-1-imidazolyl)-3-(2-bromoethylamino)-2-propanol hydrobromide as a pale yellow crystalline solid, m.p. 150°–151° C. (dec.) after drying in vacuo for 72 hours; yield 59%.

(c) A mixture containing 1-(2-nitro-1-imidazolyl)-3-(2-hydroxyethylamino)-2-propanol (RSU-1137) prepared as described by Silver et al. [Silver, A.R.J., McNeil, S.S., O'Neill, P., Jenkins, T.C. and Ahmed, I., *Biochemical Pharmacology* 1986 35 3923–3928] (2.30 g, 10.0 mmol) and dimethylbromo-sulphonium bromide (2.22 g, 10.0 mmol) prepared by the method of Furukawa et al. [Furukawa, N., Inoue, T., Aida, T. and Oae, S., *J. Chem. Soc. Chem. Commun.* 1973 212] in N,N-dimethylformamide (20 cm$^3$) was stirred at 50° C. for 12 hours. The reaction mixture was concentrated in vacuo, digested in ethanol (10 cm$^3$) and separated by preparative column chromatography using silica gel as the stationary phase and chloroform-methanol (9:1 v/v) as eluant. 1-(2-Nitro-1-imidazolyl)-3-(2-bromoethylamino)-2-propanol hydrobromide (0.68 g, 18.2%) was obtained as a yellow solid, m.p. 148.5°–150.5° C. after treatment of the eluate with ethereal hydrogen bromide.

EXAMPLE 3

1-(2-Nitro-1-imidazolyl)-3-(2-iodoethylamino)-2-propanol (RB-6146)

In a manner analogous to that described in Example 1(b) there was obtained by reaction of 1-(2-nitro-1-imidazolyl)-3-(1-aziridino)-2-propanol with aqueous hydriodic acid (57% w/w HI) at 0°–5° C. and recrystallisation from water, 1-(2-nitro-1-imidazolyl)-3-(2-iodoethylamino)-2-propanol hydriodide as a yellow microcrystalline solid, m.p. 172°–173° C. (dec.) after drying in vacuo; yield 51%.

Analysis for C$_8$H$_{14}$N$_4$O$_3$I$_2$ (M=468.04):
Calculated: C: 20.53; H: 3.02; N: 11.97; I: 54.23%,
Found: C: 21.02; H: 3.11; N: 12.12; I: 53.26%.

EXAMPLE 4

1-(2-Nitro-1-imidazolyl)-3-(2-fluoroethylamino)-2-propanol (RB-6159)

(a) A mixture of 1-(2,3-epoxypropyl)-2-nitroimidazole prepared by the method described by Beaman et al. [Beaman, A.G., Tautz, W. and Duschinsky, R., 1968; Studies in the Nitroimidazole Series. III, *Antimicrobial Agents and Chemotherapy*, pp. 520–530] (4.00 g, 23.7 mmol), 2-fluoro-ethylammonium chloride (5.00 g, 50.2 mmol) and sodium hydroxide (2.00 g, 50.0 mmol) in ethanol (60 cm$^3$) was stirred at 15° C. for 30 minutes then heated under reflux for 3 hours. The reaction mixture was then treated with decolourising charcoal (0.5 g), cooled and filtered. Concentration under reduced pressure afforded a pale yellow oil which was dissolved in ethanol (20 cm$^3$) and treated with a small excess of anhydrous ethereal hydrogen chloride to give 1-(2-nitro-1-imidazolyl)-3-(2-fluoroethylamino)-2-propanol hydrochloride in the form of a pale yellow crystalline solid (4.38 g, 68.9%) after recrystallisation from aqueous ethanol, m.p. 178°–179° C. (dec. after drying in vacuo).

Analysis for C$_8$H$_{14}$N$_4$O$_3$FCl (M=268.67):
Calculated: C: 35.76; H: 5.25; N: 20.85; F: 7.07; Cl: 13.20%,
Found: C: 35.41; H: 5.17; N: 20.65; F: 6.90; Cl: 13.38%.

(b) In a manner analogous to that described in Example 1(b) there was obtained by reaction of 1-(2-nitro-1-imidazolyl)-3-(1-aziridino)-2-propanol with aqueous hydrofluoric acid (48% w/w HF) at 0°–5° C., 1-(2-nitro-1-imidazolyl)-3-(2-fluoroethylamino)-2-propanol hydrochloride after stirring with cold ethanolic sodium hydroxide (1.0 mol equivalent) and decolourising charcoal for 15 minutes, filtration and treatment with a small excess of ethereal hydrogen chloride; yield 41%, m.p. 177°–179° C. (dec.).

EXAMPLE 5

1-(2-Nitro-1-imidazolyl)-3-(2-acetoxyethylamino)-2-propanol

A solution of 1-(2-nitro-1-imidazolyl)-3-(1-aziridino)-2-propanol (2.12 g, 10.0 mmol) in acetone (20 cm$^3$) prepared as described in Example 1(a) was treated with ethanoic acid (2.5 mol equivalents) at 25° C. then warmed to 50° C. for 15 minutes. The resulting mixture was cooled to 20° C., stirred with decolourising charcoal (0.3 g) and excess anhydrous potassium carbonate for 30 minutes, filtered and concentrated under reduced pressure to give 1-(2-nitro-1-imidazolyl)-3-(2-acetoxyethylamino)-2-propanol (1.58 g, 58.0%) in the form of a pale yellow crystalline solid.

EXAMPLE 6

1-(2-Nitro-1-imidazolyl)-3-(2-trifluoroacetoxyethylamino)-2-propanol

In a manner analogous to that described in example 5 there was obtained from reaction of 1-(2-nitro-1-imidazolyl)-3-(1-aziridino)-2-propanol with trifluoroethanoic acid, 1-(2-nitro-1-imidazolyl)-3-(2-trifluoroacetoxyethylamino)-2-propanol as a yellow oil; yield 43%.

EXAMPLE 7

1-(2-Methyl-4-nitro-1-imidazolyl)-3-(2-chloroethylamino)-2-propanol

In a manner analogous to that described in Example 1(b) there was obtained by condensation of 1-(2-methyl-4-nitro-1-imidazolyl)-3-(1-aziridino)-2-propanol [Adams, G.E., Ahmed, I., Gibson, D. and Stratford, I.J., GB-A-2123816; Ahmed, I., Jenkins, T.C., Walling, J.M., Stratford, I.J., Sheldon, P.W., Adams, G.E. and Fielden, E.M., *Int. J. Radiat. Oncol. Biol. Phys.* 1986 12 1079–1081] with aqueous hydrochloric acid at 0–5° C., 1-(2-methyl-4-nitro-1-imidazolyl)-3-(2-chloroethylamino)-2-propanol hydrochloride as very pale yellow prisms, after recrystallisation from ethanol and drying in vacuo; yield 67%.

Analysis for C$_9$H$_{16}$N$_4$O$_3$Cl$_2$ (M=299.16):

Calculated: C: 36.13; H: 5.39; N: 18.73; Cl: 23.70%,
Found: C: 35.89; H: 5.47; N: 18.86; Cl: 24.04%.

EXAMPLE 8

1-(2-Methyl-4-nitro-1-imidazolyl)-3-(2-bromoethylamino)-2-propanol

In a manner analogous to that described in Example 2(b) there was obtained by reaction of 1-(2-methyl-4-nitro-1-imidazolyl)-3-(1-aziridino)-2-propanol with excess aqueous hydrobromic acid at 0°-5° C., 1-(2-methyl-4-nitro-1-imidazolyl)-3-(2-bromoethylamino)-2-propanol hydrobromide as a cream-coloured microcrystalline solid; yield 45%.

EXAMPLE 9

1-(2-Methyl-4-nitro-1-imidazolyl)-3-(2-iodoethylamino)-2-propanol

In a manner analogous to that described in example 3 there was obtained by condensation of 1-(2-methyl-4-nitro-1-imidazolyl)-3-(1-aziridino)-2-propanol with aqueous hydriodic acid, 1-(2-methyl-4-nitro-1-imidazolyl)-3-(2-iodoethylamino)-2-propanol hydriodide as a yellow crystalline solid; yield 52%.

EXAMPLE 10

1-(2-Methyl-5-nitro-1-imidazolyl)-3-(2-haloethylamino-2-propanol: (halo=Cl,Br, I or F)

These compounds are preparable as the acid salts by reaction of 1-(2-methyl-5-nitro-1-imidazolyl)-3-(1-aziridino)-2-propanol prepared by the method of Adams et al. [Adams, G.E., Ahmed, I., Gibson, D. and Stratford, I.J., GB-A-2123816; Ahmed, I., Jenkins, T.C., Walling, J.M., Stratford, I.J., Sheldon, P.W., Adams, G.E. and
. Phys. 1986 12 Fielden, E.M., *Int. J. Radiat. Oncol. Biol. Phys.* 1986 12 1079-1081] with the appropriate aqueous hydrohalic acid or anhydrous hydrogen halide in either acetone or ethanol solution at 0-5° C., following the procedures described in Examples 1-4, by analogy with the processes described in Examples 8 to 10.

EXAMPLE 11

1-(3-Nitro-1,2,4-triazol-1-yl)-3-(2-chloroethylamino)-2-propanol

In a manner analogous to that described in Example 1(b) there was obtained by treatment of 1-(3-nitro-1,2,4-triazol-1-yl)-3-(1-aziridino)-2-propanol [Shibamoto, Y., Sakano, K., Kimura, R., Nishidai, T., Nishimoto, S.-I., Ono, K., Kagiya, T. and Abe, M. *Int. J. Radiat. Oncol. Biol. Phys.* 1986 12 1063-1066] with aqueous hydrochloric acid at 25° C., 1-(3-nitro-1,2,4-triazol-1-yl)-3-(2-chloroethylamino)-2-propanol hydrochloride as colourless prisms, m.p. 179-180° C.; yield 85%.

Analysis for $C_7H_{13}N_5O_3Cl_2$ (M=286.12):
Calculated: C: 29.39; H: 4.58; N: 24.48; Cl: 24.78%,
Found: C: 29.62; H: 4.83; N: 24.74; Cl: 24.18%.

EXAMPLE 12

1-(3-Nitro-1,2,4-triazol-1-yl)-3-(2-bromoethylamino)-2-propanol

In a manner analogous to that described in Example 2(b) there was obtained by reaction of 1-(3-nitro-1,2,4-triazol-1-yl)-3-(1-aziridino)-2-propanol with aqueous hydrobromic acid, 1-(3-nitro-1,2,4-triazol-1-yl)-3-(2-bromoethylamino)-2-propanol hydrobromide in the form of hygroscopic colourless prisms, m.p. 128°-129° C.; yield 63%.

Analysis for $C_7H_{13}N_5O_3Br_2$ (M=375.03):
Calculated: C: 22.42; H: 3.49; N: 18.67; Br: 42.61%,
Found: C: 22.59; H: 3.52; N: 19.08; Br: 42.06%.

EXAMPLE 13

1-(2-Nitro-1-imidazolyl)-3-(3-bromopropylamino)-2-propanol

A solution containing 3-bromopropylammonium bromide (6.47 g, 29.6 mmol) and sodium hydroxide (1.18 g, 29.5 mmol) in ethanol (40 cm$^3$) was stirred at 20° C.; after 1 hour, diethyl ether (40 cm$^3$) was added and the mixture filtered. 1-(2,3-epoxypropyl)-2-nitroimidazole (5.00 g, 29.6 mmol) was added to the filtrate and the solution heated to reflux for 45 minutes. The reaction mixture was then treated with decolourising charcoal (0.5 g), filtered, concentrated under reduced pressure and treated with aqueous hydrobromic acid (48% w/w HBr, 2.0 cm$^3$). The solid which appeared upon refrigeration was recrystallised from aqueous ethanol to give 1-(2-nitro-1-imidazolyl)-3-(3-bromopropylamino)-2-propanol hydrobromide (6.87 g, 59.9%) as a hygroscopic yellow crystalline solid.

EXAMPLE 14

1-(2-Nitro-1-imidazolyl)-3-(1-chloro-2-methyl-2-propylamino)-2-propanol

In a manner analogous to that described in Example 1(b) there was obtained following condensation of 1-(2-nitro-1-imidazolyl)-3-(2,2-dimethyl-1-aziridino)-2-propanol prepared by the method described by Adams et al. [Adams, G.E., Ahmed, I., Gibson, D. and Stratford, I.J., GB-A-2123816] with aqueous hydrochloric acid at 40° C., 1-(2-nitro-1-imidazolyl)-3-(1-chloro-2-methyl-2-propylamino)-2-propanol hydrochloride as colourless prisms, m.p. 196.5°-198° C. (dec.) after recrystallisation from aqueous acetone containing 0.5% v/v aqueous hydrochloric acid; yield 78%.

Analysis for $C_{10}H_{18}N_4O_3Cl_2$ (M=313.19):
Calculated: C: 38.35; H: 5.79; N: 17.89; Cl: 22.64%,
Found: C: 38.24; H: 5.85; N: 17.82; Cl: 22.41%.

EXAMPLE 15

1-(2-Nitro-1-imidazolyl)-3-(1-bromo-2-methyl-2-propylamino)-2-propanol

In a manner analogous to that described in Example 2(b) there was obtained from reaction of 1-(2-nitro-1-imidazolyl)-3-(2,2-dimethyl-1-aziridino)-2-propanol with aqueous hydrobromic acid at 40° C., 1-(2-nitro-1-imidazolyl)-3-(1-bromo-2-methyl-2-propylamino)-2-propanol hydrobromide as very pale yellow prisms, m.p. 186°-187° C. (dec.); yield 82%

Analysis for $C_{10}H_{18}N_4O_3Br_2$ (M=402.10):
Calculated: C: 29.87; H: 4.51; N: 13.93; Br: 39.75%,
Found: C: 29.92; H: 4.58; N: 13.91; Br: 39.23%.

EXAMPLE 16

1-(2-Nitro-1-imidazolyl)-3-(dl-threo-2-chloro-3-butylamino)-2-propanol

In a manner analogous to that described in Example 1(b) there was obtained by condensation of 1-(2-nitro-1-imidazolyl)-3-(cis-2,3-dimethyl-1-aziridino)-2-propanol prepared by the method described by Adams et al. [Adams, G.E., Ahmed, I., Gibson, D. and Stratford, I.J., GB-A-2123816] with aqueous hydrochloric acid at 20° C., 1-(2-nitro-1-imidazolyl)-3- (dl-threo- 2-chloro-3-butylamino)-2-propanol hydrochloride as colourless prisms, m.p. 138.5°-139° C. (dec.) after recrystallisation from ethanol; yield 73%.

EXAMPLE 17

1-(2-Nitro-1-imidazolyl)-3-(dl-threo-2-bromo-3-butylamino)-2-propanol

In a manner analogous to that described in Example 2(b) there was obtained by reaction of 1-(2-nitro-1-imidazolyl)-3-(cis-2,3-dimethyl-1-aziridino)-2-propanol with aqueous hydrobromic acid at 20° C., 1-(2-nitro-1-imidazolyl)-3-(dl-threo-2-bromo-3-butylamino)-2-propanol hydrobromide as pale yellow prisms, m.p. 143°-144° C. (dec.); yield 78%.

EXAMPLE 18

1-(2-Nitro-1-imidazolyl)-3-(2-chloro-2,3-dimethyl-3-butylamino)-2-propanol

In a manner analogous to that described in Example 1(b) there was obtained by reaction of 1-(2-nitro-1-imidazolyl)-3-(2,2,3,3-tetramethyl-1-aziridino)-2-propanol synthesised by the general method outlined by Ahmed et al. [Ahmed, I., Jenkins, T.C., Walling, J.M., Stratford, I.J., Sheldon, P.W., Adams, G.E. and Fielden, E.M., *Int. J. Radiat. Oncol. Biol. Phys.* 1986 12 1079–1081] with excess aqueous hydrochloric acid at 20° C., 1-(2-nitro-1-imidazolyl)-3-(2-chloro-2,3-dimethyl-3-butylamino)-2-propanol hydrochloride as a colourless microcrystalline solid, m.p. 183°-184° C. (dec.) after recrystallisation from aqueous acetone; yield 61%.

EXAMPLE 19

1-(2-Nitro-1-imidazolyl)-3-(2-bromo-2,3-dimethyl-3-butylamino)-2-propanol

In a manner analogous to that described in Example 2(b) there was obtained following condensation of 1-(2-nitro-1-imidazolyl)-3-(2,2,3,3-tetramethyl-1-aziridino)-2-propanol with aqueous hydrobromic acid, 1-(2-nitro-1-imidazolyl)-3-(2-bromo-2,3-dimethyl-3-butylamino)-2-propanol hydrobromide as pale yellow prisms, m.p. 163°-164° C. (dec.) after evaporation to low volume and recrystallisation from aqueous acetone; yield 56%.

Analysis for $C_{12}H_{22}N_4O_3Br_2$ (M=430.15):
Calculated: C: 33.51; H: 5.16; N: 13.03; Br: 37.15%,
Found: C: 33.80; H: 5.28; N: 12.79; Br: 36.83%.

EXAMPLE 20

1-(2-Nitro-1-imidazolyl)-3-(1-bromo-2-methyl-2-propylamino)-2-propanol (a) In a manner analogous to the method described by Silver et al. [Silver, A.R.J., McNeil, S.S., O'Neill, P., Jenkins, T.C. and Ahmed, I., *Biochemical Pharmacology* 1986 35 3923–3928], 1-(2-nitro-1-imidazolyl)-3-(1-hydroxy-2-methyl-2-propylamino)-2-propanol was obtained as very pale yellow prisms, m.p. 114.5°-115.5° C. after recrystallisation from ethanol; yield 81%.

(b) A mixture containing the alcohol prepared as described in (a) above (2.58 g, 10.0 mmol), N-bromosuccinimide (2.67 g, 15.0 mmol) and triphenylphosphine (3.93 g, 15.0 mmol) in N,N-dimethylformamide (50 cm³) was stirred at 50° C. for 1.5 hours. The reaction mixture was then concentrated under reduced pressure, digested in ethanol (20 cm³), filtered and separated by preparative column chromatography using silica gel as the stationary phase and chloroform-methanol (9:1 v/v) as eluant. 1-(2-Nitro-1-imidazolyl)-3-(1-bromo-2-methyl-2-propylamino)-2-propanol hydrobromide was obtained as a yellow crystalline solid (1.09 g, 27.1%), m.p. 181°-184° C. (dec) after treatment of the eluate with a small excess of ethereal hydrogen bromide.

EXAMPLE 21

Sensitisation and Toxicity (a) C3H mice in which the KHT tumour had been implanted subcutaneously were administered RB-6145 (Example 2) intraperitoneally before treatment with radiation. The time before such treatment at which the drug was administered was such that maximum enhancement was effected. The results of such treatment are set out in Table 1 with comparison to misonidazole (MISO), etanidazole (SR 2508) and pimonidazole (Ro 03-8799). In Table 2 comparison is made with 1-(2-nitro-1-imidazolyl)-3-(1-aziridino)-2-propanol (RSU-1069). All compounds were administered in phosphate buffered saline (PBS) at pH 7.4 except RB-6145 which was administered in PBS at pH 5.4.

TABLE 1

| | Survival of KHT tumour cells following treatment with sensitiser at a dose of 200 mg/kg and 10 Gy X-rays | | | | |
|---|---|---|---|---|---|
| | NONE | MISO | SR 2508 | Ro03-8799 | RB-6145 |
| surviving fraction | $3 \times 10^{-2}$ | $1.2 \times 10^{-2}$ | $1.1 \times 10^{-2}$ | $3 \times 10^{-2}$ | $1.8 \times 10^{-3}$ |
| enhancement ratio | 1.0 | 1.5 | 1.6 | 1.0 | 2.7 |

TABLE 2

| Survival of KHT tumour cells following treatment with sensitiser and 10 Gy X-rays | | | | | |
|---|---|---|---|---|---|
| RB-6145 (Example 2) | | | RSU-1069 | | |
| Dose | | | Dose | | |
| mmol kg$^{-1}$ | (mg/kg) | surviving fraction | mmol kg$^{-1}$ | (mg/kg) | surviving fraction |
| 0.80 | 300 | $1.4 \times 10^{-3}$ | 0.38 | 80 | $1.6 \times 10^{-3}$ |
| 0.53 | 200 | $1.8 \times 10^{-3}$ | 0.26 | 50 | $3.2 \times 10^{-3}$ |
| 0.27 | 100 | $5.2 \times 10^{-3}$ | 0.14 | 30 | $4.0 \times 10^{-3}$ |
| 0.13 | 50 | $7.6 \times 10^{-3}$ | 0.04 | 8 | $7.6 \times 10^{-3}$ |

The surviving fraction for 10 Gy alone is $3 \times 10^{-2}$. The maximum does used was the maximum tolerated dose (MTD). Much higher doses of RB-6145 can be used but on a dose-for-dose basis it is the same as RSU-1069 as a sensitiser.

(b) Sensitisation and toxicity data for some of the compounds described in the above Examples are given in Table 3.

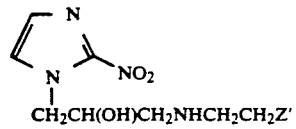

$CH_2CH(OH)CH_2NHCH_2CH_2Z'$

TABLE 3

| EXAMPLE | Compound Z' | $C_{Air}^{(a)}/$ mmol dm$^{-3}$ | $C_{N2(a)}/$ mmol dm$^{-3}$ |
|---|---|---|---|

| | | TABLE 3-continued | | | |
|---|---|---|---|---|---|
| — | RSU-1137 | OH | 70 | 3.5 | |
| 4 | RB-6159 | F | 35 | 2.5 | |
| 1 | RB-6144 | Cl | 5 | 0.35 | |
| 2 | RB-6145 | Br | 2.3 | 0.09 | |
| 3 | RB-6146 | I | 2.4 | 0.08 | |
| EXAMPLE | $C_{Air}/C_{N_2}$ | $(b)C_{1.6}/$ mmol dm$^{-3}$ | $(c)$in vivo sensitisation | | |
| — | 20 | 0.45 | ++ | | |
| 4 | 14 | ND | ND | | |
| 1 | 15 | 0.25 | ++ | | |
| 2 | 25 | 0.15 | +++ | | |
| 3 | 30 | 0.3 | ND | | |

$(a)$Toxicity is 3 hours at 37° C. Concentrations are those required for a surviving fraction of $10^{-1}$. Drugs were made up in full growth medium (buffered with bicarbonate) just before addition to cells.
$(b)$Drugs made up in PBS at pH 7.4 just before addition to cells.
$(c)$Scoring system:
++++ equal or greater efficiency than RSU-1069
+++ less than RSU-1069 but greater than MISO
++ equal to MISO
+ less than MISO
ND = not determined.

We claim:

1. A compound of formula (B):

$$XCH_2(CHOH)_nCH_2N-\underset{\underset{R'_3}{|}}{\overset{\overset{R'_2}{|}}{C}}-(CH_2)_m-\underset{\underset{R'_5}{|}}{\overset{\overset{R'_4}{|}}{C}}-Z' \quad (B)$$

with R'₁ shown on the left of the nitrogen.

wherein
is one of the groups

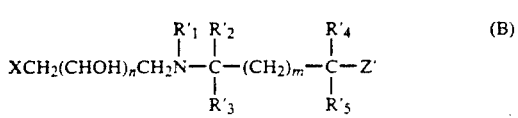

wherein R is hydrogen or an alkyl group, with a one-electron reduction potential at pH 7 of from −250 to −500 mV;
each of R'₁ to R'₅ independently represents hydrogen or an alkyl, hydroxyalkyl, aryl, aralkyl or alkaryl group;
m is 0 or 1;
n is 1 or 2; and
Z' represents a leaving group which has the potential for expulsion via an intramolecular cyclization reaction and which is selected from the group consisting of halogen; $-OCOR_6$, $-OSOR_6$, $-OSO_2R_6$, $OPO_3(R_6)_2$ or $-OP(O)(N(R_6)_2)_2$ where $R_6$ is hydrogen, alkyl, haloalkyl, phenyl, aralkyl, thioalkyl, acyl or amino; aryloxy, $-ONO_2$, $-NHSO_2R_7$, $-NHCOR_7$, $-NHCO_2R_7$, $-N(COR_7)_2$ or cyclic imide where $R_7$ is hydrogen, alkyl, phenyl or aralkyl; and $-N^+R^aR^bR^c$ or $-N(O)R^aR^b$ where $R^a$ to $R^c$ are independently alkyl;
or a physiologically acceptable acid addition salt thereof;
with the proviso that m is 1 where X represents

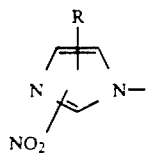

in which R is hydrogen or an alkyl group, R'₁ is hydrogen, each of R'₂ to R'₅ independently represents hydrogen, alkyl, aryl, aralkyl or alkaryl and Z' represents halogen.

2. A compound according to claim 1, wherein X represents an imidazol-1-yl group having a nitro group in the 2-position or a 1,2,4-triazol-1-yl group having a nitro group in the 3-position.

3. A compound according to claim 1, wherein m is 0.

4. A compound according to claim 1, wherein n is 1.

5. A compound according to claim 1, wherein each of R'₁ to R'₅ independently represents hydrogen or C₁-C₆ alkyl.

6. A compound according to claim 5, wherein R'₁ is hydrogen and each of R'₂ and R'₅ is independently hydrogen or methyl.

7. A compound according to claim 1, wherein Z' is a halogen or acyloxy unsubstituted or substituted by a halogen.

8. A compound according to claim 1, which is in the form of a salt with hydrochloric, hydrobromic or hydriodic acid.

9. A compound according to claim 1, which is selected from the group consisting of:
1-(2-nitro-1-imidazolyl)-3-(2-acetoxyethylamino)-2-propanol,
1-(2-nitro-1-imidazolyl)-3-(2-trifluoroacetoxyethylamino)-2-propanol,
1-(3-nitro-1,2,4-triazol-1-yl)-3-(2-chloroethylamino)-2-propanol hydrochloride,
1-(3-nitro-1,2,4-triazol-1-yl)-3-(2-bromoethylamino)-2-propanol hydrobromide, and
1-(2-nitro-1-imidazolyl)-3-(3-bromopropylamino)-2-propanol hyrobromide.

10. A compound selected from the group consisting of:
1-(2-nitro-1-imidazolyl)-3-(2-chloroethylamino)-2-propanol hydrochloride,
1-(2-nitro-1-imidazolyl)-3-(2-bromoethylamino)-2-propanol hydrobromide,
1-(2-nitro-1-imidazolyl)-3-(2-iodoethylamino)-2-propanol hydriodide,
1-(2-nitro-1-imidazolyl)-3-(2-fluoroethylamino)-2-propanol hydrochloride,
1-(2-methyl-4-nitro-1-imidazolyl)-3-(2-chloroethylamino)-2-propanol hydrochloride,
1-(2-methyl-4-nitro-1-imidazolyl)-3-(2-bromoethylamino)-2-propanol hydrobromide,
1-(2-methyl-4-nitro-1-imidazolyl)-3-(2-iodoethylamino)-2-propanol hydriodide,
1-(2-methyl-5-nitro-1-imidazolyl)-3-(2-chloroethylamino)-2-propanol hydrochloride,
1-(2-methyl-5-nitro-1-imidazolyl)-3-(2-bromoethylamino)-2-propanol hydrobromide,
1-(2-methyl-5-nitro-1-imidazolyl)-3-(2-iodoethylamino)-2-propanol hydriodide,
1-(2-methyl-5-nitro-1-imidzolyl)-3-(2-fluoroethylamino)-2-propanol hydrochloride, 1-(2-nitro-1-imidazolyl)-3-(1-chloro-2-methyl-2-propylamino)-2-propanol hydrochloride, 1-(2-nitro-1-imidazolyl)-3-(1-bromo-2-methyl-2-propylamino)-2-propanol hydrobromide, 1-(2-nitro-1-imidazolyl)-3-(dl-threo-2-chloro-3-butylamino)-2-propanol hydrochloride, 1-(2-nitro-1-imidazolyl)-3-(dl-threo-2-bromo-3-butylamino)-2-propanol hydrobromide, 1-(2-nitro-1-imidazolyl)-3-(2-chloro-2,3-dimethyl-3-butylamino)-2-propanol hydrochloride, and 1-(2-nitro-1-imidazolyl)-3-(2-bromo-2,3-dimethyl-3-butylamino)-2-propanol hydrobromide.

11. A pharmaceutical composition comprising a pharmaceutically compatible carrier or diluent and, as active ingredient, a compound of formula (A):

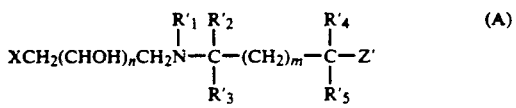

wherein

X is one of the groups

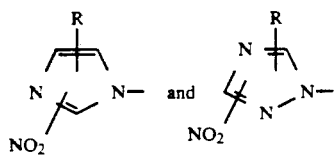

wherein R is hydrogen or an alkyl group, with a one-electron reduction potential at pH 7 of from $-250$ to $-500$ mV;

each of $R'_1$ to $R'_5$ independently represents hydrogen or an alkyl, hydroxyalkyl, aryl, aralkyl or alkaryl group;

m is 0 or 1;

n is 1 or 2; and

Z' represents a leaving group which has the potential for expulsion via an intramolecular cyclization reaction and which is selected from the group consisting of halogen; $-OCOR_6$, $-OSOR_6$, $-OSO_2R_6$, $-OPO_3(R_6)_2$ or $-OP(O)(N(R_6)_2)_2$ where $R_6$ is hydrogen, alkyl, haloalkyl, phenyl, aralkyl, thioalkyl, acyl or amino; aryloxy, $-ONO_2$, $-NHSO_2R_7$, $-NHCOR_7$, $-NHCO_2R_7$, $-N(COR_7)_2$ or cyclic imide wherein $R_7$ is hydrogen, alkyl, phenyl or aralkyl; and $-N^+R^aR^bR^c$ or $-N(O)-R^aR^b$ wherein $R^a$ to $R^c$ are independently alkyl;

or a physiologically acceptable acid addition salt thereof.

12. A composition according to claim 11, wherein X represents an imidazol-1-yl group having a nitro group in the 2-position or a 1,2,4-triazol-1-yl group having a nitro group in the 3-position.

13. A composition according to claim 11, wherein m is 0.

14. A composition according to claim 11, wherein n is 1.

15. A composition according to claim 11, wherein each of $R'_1$ to $R'_5$ independently represents hydrogen or $C_1$-$C_6$ alkyl.

16. A composition according to claim 15, wherein $R'_1$ is hydrogen and each of $R'_2$ and $R'_5$ is independently hydrogen or methyl.

17. A composition according to claim 11, wherein Z' is a halogen or acyloxy unsubstituted or substituted by a halogen.

18. A composition according to claim 11, wherein the compound of formula (A) is present in the form of a salt with hydrochloric, hydrobromic or hydriodic acid.

19. A composition according to claim 11, wherein the compound of formula (A) or salt thereof is selected from the group consisting of:

1-(2-nitro-1-imidazolyl)-3-(2-acetoxyethylamino)-2-propanol, 1-(2-nitro-1-imidazolyl)-3-(2-trifluoroacetoxyethylamino)-2-propanol, 1-(3-nitro-1,2,4-triazol-1-yl)-3-(2-chloroethylamino)-2-propanol hydrochloride, 1-(3-nitro-1,2,4-triazol-1-yl)-3-(2-bromoethylamino)-2-propanol hydrobromide, and 1-(2-nitro-1-imidazolyl)-3-(3-bromopropylamino)-2-propanol hydrobromide.

20. A composition according to claim 11, wherein the compound of formula (A) or salt thereof is selected from the group consisting of:

1-(2-nitro-1-imidazolyl)-3-(2-chloroethylamino)-2-propanol hydrochloride, b   1-(2-nitro-1-imidazolyl)-3-(2-bromoethylamino)-2-propanol hydrobromide, 1-(2-nitro-1-imidazolyl)-3-(2-iodoethylamino)-2-propanol hydriodide, 1-(2-nitro-1-imidazolyl)-3-(2-fluoroethylamino)-2-propanol hydrochloride, 1-(2-methyl-4-nitro-1-imidazolyl)-3-(2-chloroethylamino)-2-propanol hydrochloride, 1-(2-methyl-4-nitro-1-imidazolyl)-3-(2-bromoethylamino)-2-propanol hydrobromide, 1-(2-methyl-4-nitro-1-imidazolyl)-3-(2-iodoethylamino)-2-propanol hydriodide, 1-(2-methyl-5-nitro-1-imidazolyl)-3-(2-chloroethylamino)-2-propanol hydrochloride, 1-(2-methyl-5-nitro-1-imidazolyl)-3-(2-bromoethylamino)-2-propanol hydrobromide, 1-(2-methyl-5-nitro-1-imidazolyl)-3-(2-iodoethylamino)-2-propanol hydriodide, 1-(2-methyl-5-nitro-1-imidazolyl)-3-(2-fluoroethylamino)-2-propanol hydrochloride, 1-(2-nitro-1-imidazolyl)-3-(1-chloro-2-methyl-2-propylamino)-2-propanol hydrochloride, 1-(2-nitro-1-imidazolyl)-3-(1-bromo-2-methyl-2-propylamino)-2-propanol hydrobromide, 1-(2-nitro-1-imidazolyl)-3-(dl-threo-2-chloro-3-butylamino)-2-propanol hydrochloride, 1-(2-nitro-1-imidazolyll)-3-(dl-threo-2-bromo-3-butylamino)-2-propanol hydrobromide, 1-(2-nitro-1-imidazolyl)-3-(2-chloro-2,3-dimethyl-3-butylamino)-2-propanol hydrochloride, and 1-(2-nitro-1-imidazolyl)-3-(2-bromo-2,3-dimethyl-3-butylamino)-2-propanol hydrobromide.

* * * * *